United States Patent [19]

Guirgis

[11] 4,152,208

[45] May 1, 1979

[54] STABILIZED LEUCOCYTES

[75] Inventor: Hoda A. Guirgis, Omaha, Nebr.

[73] Assignee: Hoffmann-La Roche Inc., Nutley, N.J.

[21] Appl. No.: 858,129

[22] Filed: Dec. 6, 1977

Related U.S. Application Data

[63] Continuation-in-part of Ser. No. 782,597, Mar. 29, 1977, abandoned.

[51] Int. Cl.$^2$ .................... C12K 9/00; A61K 35/14
[52] U.S. Cl. .................................... 195/1.8; 424/101
[58] Field of Search ........................ 424/101; 195/1.8

[56] References Cited

U.S. PATENT DOCUMENTS 4,004,975  1/1977  Lionetti et al. ................... 195/1.8

OTHER PUBLICATIONS

Chisari et al., The J. of Experimental Med., vol. 142, (1975), pp. 1092 and 1093.
Chang et al., Biochemical and Biophysical Research Communications, vol. 64, No. 2, (1975), pp. 539 and 540.

Primary Examiner—Sam Rosen
Attorney, Agent, or Firm—Jon S. Saxe; George M. Gould; R. Hain Swope

[57] ABSTRACT

The viability of leukocytes or specific fractions of leukocytes is maintained by drawing blood from a donor or patient into a mixture of an anticlotting agent and a basic salt solution (BSS) or a minimum essential medium (MEM) which solution or medium sustains the viability of the leukocytes in the blood, then layering the blood-MEM or BSS mixture on a Ficoll-Hypaque solution and centrifuging to separate the leukocytes. The resulting leukocytes are diluted to about $0.5 \times 10^6$ viable cells per ml. in BSS or MEM containing antibiotics and fetal calf serum or serum substitutes equivalent thereto. The resulting suspension is transferred into sterile containers at room temperature so that each container has about $2-10 \times 10^6$ cells. The containers are then packed into insulated containers and are ready for shipping.

5 Claims, No Drawings

STABILIZED LEUCOCYTES

RELATED APPLICATIONS

This application is a continuation-in-part of U.S. Patent Application Ser. No. 782,597, filed Mar. 29, 1977, now abandoned.

BACKGROUND

Leukocytes are important for research and are utilized in various medical and medical diagnostic applications. Problems occur when it is necessary or desired to snip leukocytes from one location to another. Generally, leukocytes heretofore had been shipped cold, e.g., about 4° C., because they are unstable at warmer temperatures such as room temperatures unless used within five to six hours of their separation from whole blood.

Methods of collecting blood from donors or patients and separating leukocytes therefrom have been, until the invention described herein, unsatisfactory for forming suspensions of leukocytes or specific fractions thereof which are stable at room temperature for extended periods. The usual method is to collect or place the blood into a syringe or container containing sufficient heparin to prevent clotting, separate the leukocytes and suspend them in a buffered medium. Another method comprises collecting blood, defibrinating it with glass beads and separating the granulocytes by magnetic particles to leave the lymphocytes in the supernatant. Still another technique comprises placing collected blood in Hank's solution containing sufficient heparin to provide 30 units/ml. of blood. This latter method is about half as effective in maintaining viability compared to drawing blood directly into BSS- or MEM-heparin solution as in the invention described herein.

The above and other known methods of separating leukocytes from blood do not result in a suspension of leukocytes which can be shipped from one location to another at temperatures substantially above 4° C., e.g., room temperature. There is thus a need for a stable suspension of leukocytes which can be shipped at temperatures which may vary from about 4° C. to about 30° C. and still remain viable for several days.

STATEMENT OF PRIOR ART

The following references of which applicant is aware are considered to have some pertinency to the subject invention.

Pattengale et al., The New England Journal of Medicine 291, No. 22, 1145-48, Nov. 28, 1974 describes separating of leukocytes from heparinized blood, followed by lysis of the red cells and resuspending of the leukocytes in a suitable medium containing 10% fetal bovine serum.

Schumm et al., Europ. J. Cancer 10, 107-113 (1974) also disclose drawing blood into heparinized vials, isolating the leukocytes and suspending them in Hank's medium.

Zucker-Franklin et al., Proc. Nat. Acad. Sci. USA 71, No. 7, 2711-2714 describe obtaining purified leukocytes from heparinized blood which are then suspended in suitable medium containing 15% fetal calf serum.

Mecker et al., Oncology 30, 177-191 (1974) describe a method wherein blood is collected in Hank's solution containing sufficient heparin to provide 30 units/ml of blood.

Chisari et al., The Journal of Experimental Medicine 142, 1092-1107 (1975) describe the conventional technique of layering leukocytes on a Ficoll-Hypaque barrier. The reference further teaches suspending leukocytes in a suitable medium supplemented with antibiotics, i.e. penicillin and streptomycin.

Boyum, Scand. J. Clin. Lab. Invest. 21 (Suppl.) 97, 77 (1968) describes a method of isolating leukocytes wherein blood is collected in a heparinized syringe, diluted with phosphate buffer and centrifuged on a layer of Ficoll-Hypaque.

Chang et al., Biochemical and Biophysical Research Communications 64, No. 2, 539-545 (1975) is similar to Chisari in that it discloses blood being drawn into heparinized syringes, treated to purify the leukocytes which are then suspended in a suitable medium containing 20% heat-inactivated fetal calf serum, penicillin and streptomycin.

West et al., Clinical Immunology and Immunopathology 5, 60-66 (1976) describe purification of leukocytes according to the method of Boyum, supra, and mixing of the leukocytes with heat-inactivated fetal calf serum.

Muijsson et al., Biochemical Genetics 13, Nos. 7/8, 501-509 (1975) describe preparation of leukocytes by a method very similar to those described above, i.e. drawning blood into heparinized saline, layering the leukocytes on Ficoll-Hypaque, centrifuging and resuspending the leukocytes in a suitable medium.

Vanky et al., J. Nat. Cancer Inst. 47, No. 1, 95-103 (July, 1971) teaches a method of defibrinating blood with glass beads and separating granulocytes by magnetic particles.

Lionetti et al., U.S. Pat. No. 4,004,975, teache a method of preserving granulocytes which includes the isolation and freezing of the leukocytes.

None of these references teaches nor suggests a means whereby leukocytes can be maintained in a viable state for a period of several days at temperatures substantially in excess of 4° C.

DESCRIPTION OF THE INVENTION

This invention is directed to a method by which a temperature stable leukocyte suspension is produced and the resulting suspension which is suitable for shipping from one location to another at temperatures above 4° C.

The process of this invention is generally applicable to all leukocytes, e.g., macrophages, neutrophils, eosinophils, basophils, lymphocytes and the like. The preferred embodiment of the process of this invention is applicable to lymphocytes.

The process of this invention is carried out by the following means:

(a) collecting blood from a donor or patient directly into a syringe or other container which contains an anticlotting agent and a medium which sustains the viability of the leukocytes, i.e., a basic salt solution (BSS) which may or may not contain added amino acids and vitamins; or a minimal essential medium (MEM), then mixed. It is important to the success of this invention that the blood be drawn directly into the BSS- or MEM-heparin mixture. Any other means of combining the materials achieves unsatisfactory results because the resulting leukocytes lose viability. For example, the viability of lymphocytes in suspension produced by the process of this invention is about 90% to 100% for about a week at room temperature while analogous processes result in about one-half the viability of lymphocytes.

Suitable anticlotting agents are EDTA, sodium fluoride, sodium citrate, heparin and the like, preferred for use in this invention is heparin. The amount of anticlotting agent used can vary with the volume of blood in the sample, but it should be sufficient to insure that no clotting occurs. When heparin is used, for example, approximately 20 USP units of heparin per ml. of blood, depending on the specific heparin used is sufficient.

The amount of BSS or MEM used should be sufficient to insure that the leukocytes in the blood remain viable. Usually about 30%–50% by volume, based on the blood volume, of the BSS or MEM is used. Various BSS or MEM formulations are suitable for use in this invention. Some of the common commercial BSS's and MEM's are as follows: Earle's MEM, Hanks' MEM, RPMI medium, F-13 medium, Hanks' F-12 medium, Hanks' F-10 medium, MB75211, McCoy 5a medium, Medium 499, Medium L-15, NCTC 109, Scherers Maintenance Solution, Earle's Basic Salt Solution, Hanks' Basic Salt Solution, Gey's Basic Salt Solution.

Typical MEM and BSS solutions have the following formulations:

Eagle Minimum Essential Medium
Eagle, H. Science 130, 432, (1959)]

Minimum Essential Medium (Eagle)

| Components | mg./liter |
|---|---|
| Amino Acids | |
| L-Arginine . HCl | 126.4 |
| L-Cystine | 24.0 |
| L-Glutamine | 292.0 |
| L-Histidine . HCl . H$_2$O | 41.9 |
| L-Isoleucine | 52.5 |
| L-Leucine | 52.4 |
| L-Lysine . HCl | 73.1 |
| L-Methionine | 14.9 |
| L-Phenylalanine | 33.0 |
| L-Theronine | 47.6 |
| L-Tryptophan | 10.2 |
| L-Tyrosine | 36.2 |
| L-Valine | 46.8 |
| Vitamins | |
| D-Ca-Pantothenate | 1.0 |
| Choline Chloride | 1.0 |
| Folic Acid | 1.0 |
| i-Inositol | 2.0 |
| Nicotinamide | 1.0 |
| Pyridoxal . HCl | 1.0 |
| Riboflavin | 0.1 |
| Thiamine . HCl | 1.0 |
| Inorganic Salts and Other Components | |
| Earle's BSS | |
| CaCl$_2$ . 2H$_2$O | 265.0 |
| KCl | 400.0 |
| MgSO$_4$ . 7H$_2$O | 200.0 |
| NaCl | 6800.0 |
| NaHCO$_3$ | 2200.0 |
| NaH$_2$PO$_4$ . H$_2$O | 140.0 |
| Dextrose | 1000.0 |
| Phenol Red | 10.0 |
| Components | |
| Hanks' BSS | |
| CaCl$_2$ . 2H$_2$O | 186.0 |
| KCl | 400.0 |
| KH$_2$PO$_4$ | 60.0 |
| MgSO$_4$ . 7H$_2$O | 200.0 |
| NaCl | 8000.0 |
| NaHCO$_3$ | 350.0 |
| Na$_2$HPO$_4$ . 7H$_2$O | 90.0 |
| Dextrose | 1000.0 |
| Phenol Red | 20.0 |
| Suspension Medium BSS | |
| KCl | 400.0 |
| NaCl | 6800.0 |
| NaHCO$_3$ | 2200.0 |
| NaH$_2$PO$_4$ . H$_2$O | 1500.0 |
| MgCl$_2$ . 6H$_2$O | 200.0 |
| Dextrose | 1000.0 |
| Phenol Red | 10.0 |
| Non-Essential Amino Acids (NEAA) | |
| L-Alanine | 8.90 |
| L-Aspartic Acid | 13.30 |
| L-Asparagine | 13.21 |
| L-Glutamic Acid | 14.70 |
| Glycine | 7.50 |
| L-Proline | 11.50 |
| L-Serine | 10.50 |

Earle's MEM is vialed at pH 7.0 to 7.2
Hanks' MEM is vialed at pH 7.2 to 7.4.

RMPI Media 1640 [Moore et al., JAMA 199, 519–524 (1967); In Vitro 6, No. 2 (1970)]

RPMI Media 1640

| Components | mg./liter |
|---|---|
| Amino Acids | |
| L-Alanine | — |
| L-Arginine (free base) | 200.0 |
| L-Asparagine | 50.0 |
| L-Aspartic Acid | 20.0 |
| L-Cystine | 50.0 |
| L-Glutamic Acid | 20.0 |
| L-Glutamine | 300.0 |
| Glycine | 10.0 |
| L-Histidine (free base) | 15.0 |
| Hydroxy-L proline | 20.0 |
| L-Isoleucine | 50.0 |
| L-Leucine | 50.0 |
| L-Lysine . HCl | 40.0 |
| L-Methionine | 15.0 |
| L-Phenylalanine | 15.0 |
| L-Proline | 20.0 |
| L-Serine | 30.0 |
| L-Threonine | 20.0 |
| L-Tryptophan | 5.0 |
| L-Tyrosine | 20.0 |
| L-Valine | 20.0 |
| Vitamins | |
| P-Aminobenzoic aCID | 1.00 |
| Biotin | 0.20 |
| D-Ca-Pantothenate | 0.25 |
| Choline chloride | 3.00 |
| Folic Acid | 1.00 |
| i-Inositol | 35.00 |
| Nicotinamide | 1.00 |
| Pyridoxine . HCl | 1.00 |
| Riboflavin | 0.20 |
| Thiamine . HCl | 1.00 |
| Vitamin B$_{12}$ | 0.005 |
| Other Components | |
| Dextrose | 2000.0 |
| Glutathione (reduced) | 1.0 |
| Phenol Red | 5.0 |
| Inorganic Salts | |
| Ca(NO$_3$)$_2$ . 4H$_2$O | 100.0 |
| KCl | 400.0 |
| MgSO$_4$ . 7H$_2$O | 100.0 |
| NaCl | 6000.0 |
| NaHCO$_3$ | 2000.0 |
| Na$_2$HPO$_4$ . 7H$_2$O | 1512.0 | vialed at pH 7.2 to 7.4

Earle's Gey's and Hanks' Balanced Salt Solution [Earle, J. Nat. Cancer Inst. 4 165–212 (1943); Gey et al., Am. J. Cancer 27, 45–76 (1936); Hanks et al., Proc. Soc. Exp. Biol. and Med. 71 196–200 (1949)]

Balanced Salt Solutions

| Components | Earle's (mg./liter) | Gey's (mg./liter) | Hanks' (mg./liter) |
|---|---|---|---|
| NaCl | 6800 | 8000 | 8000 |
| KCl | 400 | 375 | 400 |
| CaCl$_2$ . 2H$_2$O | 265 | 225 | 186 |
| MgSO$_4$ . 7H$_2$O | 200 | 70 | 200 |
| MgCl$_2$ . 6H$_2$O | — | 210 | — |
| NaH$_2$PO$_4$ . H$_2$O | 140 | — | — |

-continued

| | | | |
|---|---|---|---|
| Na₂HPO₄ . 7H₂O | — | 226 | 90 |
| KH₂PO₄ | — | 30 | 60 |
| Dextrose | 1000 | 1000 | 1000 |
| Phenol Red | 10 | — | 20 |
| NaHCO₃ | 2200 | 227 | 350 |

These solutions are available from *Microbiological Associates*, Bethesda, Md.

It is step (a) described herein which makes it possible to perform the remaining steps of the process of this invention to achieve the stable leukocyte composition. After mixing the ingredients together the following steps are performed.

(b) The blood-heparin-MEM or BSS mixture is layered on a Ficoll-Hypaque solution in a glass container, preferably a test tube. The volume ratio of the Ficoll-Hypaque mixture to the blood is from 1:1 to 1:2, preferably 1:1. This is accomplished by carefully pouring the mixture onto the solution in the container. The relative amounts of the mixture and solution can vary, however, usually slightly more volume of mixture is used. The amounts of Ficoll and Hypaque can vary, however, the relative amounts should be such that the specific gravity of the Ficoll-Hypaque solution is about the same as the particular leukocytes being separated, for example, when lymphocytes are separated, the specific gravity should be about 1.07 to 1.08. Ficoll is a synthetic high polymer made by the copolymerization of sucrose and epichlorohydrin, average molecular weight is 400,000±100,000 and Hypaque is sodium diatrizoate. Ficoll and Hypaque are both soluble in water. Distilled and/or deionized water is used to form the Ficoll-Hypaque solution used in this invention. Ficoll is available from *Pharmacia*, Piscataway, N.J. Hypaque is available from *Winthrop Laboratories*, New York City.

(c) The blood-heparin-BSS or MEM mixture layered on the Ficoll-Hypaque solution is centrifuged at 4° C. to separate the leukocytes from the plasma. The centrifugation is carried out in the cold to insure that there is no deterioration of the leukocytes from heat caused by the centrifugation forces. The rpm of the centrifuge should be such that about 400 times gravity results for sufficient time to allow the leukocytes to layer on the Ficoll-Hypaque solution, e.g., about 30 to 40 minutes.

(d) The resulting supernatant plasma from step (c) is then decanted off and the leukocyte containing layer removed by conventional means, e.g., with a syringe. The leukocyte containing layer is then mixed with BSS or MEM and centrifuged at about 400 times gravity for a time sufficient to allow the leukocytes to separate from the BSS or MEM, e.g., about 10 to 30 minutes. The supernatant is then decanted off and the pellet which remains contains the leukocytes.

The leukocyte pellet is suspended in BSS or MEM and an aliquot is taken so the number of leukocyte cells can be counted. Any convenient means for counting the cells can be used. However, it has been found that a Coulter Counter (Coulter Electronics Inc. Hialeah, Fla. is preferred. In addition, another aliquot is used to assay for the viability of the cells. The conventional trypan blue dye exclusion method is used. The cell counting and viability assay are not part of the process of this invention but are used in commercial processes for quality control.

(e) After counting the cells and determining that they are viable, the BSS or MEM suspension is diluted with additional BSS or MEM suspension containing antibiotics and heat-inactivated fetal calf serum or a serum substitute equivalent thereto to achieve a final viable leukocyte concentration of about $0.5 \times 10^6$ viable cells per ml.

The antibiotics are added to insure the sterility of the leukocyte preparation. Usually, groups of antibiotics having varied specific activities are added to achieve a broad spectrum of activity. The amounts of given antibiotics utilized will vary with their effective concentration as is recognized in the art. For example, a preferred combination of antibiotics is penicillin, streptomycin and gentamycin. When this preferred group of antibiotics is utilized, the diluting medium contains an amount sufficient to provide concentrations of 75 units, 50 μgrams and 50 μgrams per ml, respectively, in the final preparation.

The heat-inactivated fetal calf serum of serum substitute equivalent thereto is used to maintain the leukocytes in the proper environment for viability. By this is meant that they provide protein in the media which acts to prevent loss of protein from the cell membranes, Also, the presence of the source of protein in the environment acts in a sense to nourish the cell membrane.

The use of heat-inactivated fetal calf serum as an adjunct to the maintenance of various types of cells is well documented in the art. See, for example: McCall et al., Ann. Rheum. Dis., 25, pages 42–48 (1966); McLeod et al., Blood, Vol. 44, No. 4, pages 517–534; Kovacs et al., J. of Inv. Dermatology, Vol. 63, pages 456–60 (1974); and Fabrikant et al., Radiology, Vol. 92, pages 1309–20 (1962), as well as the Zucker-Franklin et al. and Chang et al. references discussed in the Statement of Prior Art. Serum substitutes recognized as being equivalent to heat-inactivated fetal calf serum are basically of two types, i.e. protein and synthetic media. Examples of protein substitutes include human serum albumin and antologus serum. Examples of synthetic media include serum free culture systems containing as protective agents synthetic polymers such as methylcellulose, sodium carboxymethyl cellulose, dextrans, hydroxyethyl starch and the like. For a detailed discussion of such serum substitutes, see Taylor, J. of the National Cancer Institute, Vol. 53, No. 5, November, 1974, pages 1449-1457 and the references cited therein. Generally, the diluting medium, i.e. BSS or MEM, will contain from about 1% to about 10% by volume heat-inactivated fetal calf serum or a serum substitute equivalent thereto.

(f) The suspension resulting from step (e), maintained at room temperature, is then transferred into sterile containers, e.g. glass, plastic and the like for shipping. Each container should contain a convenient amount of leukocyte cells which retain substantially all their viability, i.e., about 2 to $10 \times 10^6$ leukocyte cells. The containers are packed into insulated containers and are ready for shipping. A preferred container is made from Styrofoam (foamed polystyrene).

When prepared as described, about 90% and more of the leukocyte cells in the suspension are stable for about a week.

The following example illustrates the invention.

EXAMPLE

1 Ml. heparin and 11 ml. of F-13 medium (an MEM medium) are drawn into a 30 ml. syringe. The syringe needles are changed and 18 mls. of blood from a donor are drawn directly into the syringe. The blood and heparin-F-13 media are mixed by inverting the syringe once or twice.

About 8 ml. of the resulting mixture are layered on 6 ml. of Ficoll-Hypaque solution in a 16×125 mm. test tube and centrifuged at 1000 rpm (400 times gravity) at 4° C. for 37 minutes. The resulting supernatant plasma layer is decanted off. The lymphocyte rich layer is removed and transferred to 10 ml. of F-13 media. The resulting mixture is centrifuged at 1000 rpm (400 times gravity) at 4° C. for 10 minutes. The supernatant is removed to leave a pellet containing lymphocytes. 4.5 Ml. F-13 media is added to the pellet and mixed well. A 0.1 ml. aliquot is removed and put into 20 mls. of counting solution (an isotonic solution) for a Coulter count (cell count on a Coulter Counter). Another aliquot is removed and the lymphocyte cells therein are assayed for viability using trypan blue dye exclusion method.

The suspension of lymphocytes in F-13 media is diluted to $0.5 \times 10^6$ viable cells per ml. with F-13 media containing 1000 units/ml. penicillin, 50 µg/ml. streptomycin and 10% by volume heat inactivated fetal calf serum. The resulting samples, maintained at room temperature, are transferred into sterile glass containers so that each glass container has $5 \times 10^6$ lymphocyte cells. The glass containers are packed into Styrofoam containers and are ready for shipment, e.g., by air freight. The viability of lymphocyte cells in suspension prepared according to this example and shipped by air freight was as follows:

TABLE

| Sample | Age of Cells (Days) | % Viability |
|---|---|---|
| 1 | 4 | 97 |
| 2 | 4 | 98 |
| 3 | 5 | 94 |
| 4 | 3 | 92 |
| 5 | 1 | 93 |
| 6 | 4 | 91 |

The data in the Table demonstrates the effectiveness of the process of this invention.

The Ficoll-Hypaque solution used in this example is prepared as follows:

A. Preparation of Ficoll
1. Weigh 18 grams of Ficoll.
2. Add sufficient distilled water to the Ficoll to total 200 ml.
3. Mix until all dissolved.
4. Mix for 5 minutes with a magnetic stirrer.

B. Preparation of Hypaque
1. Use 25 ml. burettes—one for distilled $H_2O$, the other for a 50% aqueous Hypaque solution.
2. Dilute 56.5 ml. of the 50% Hypaque solution with 26.84 ml. of distilled $H_2O$.
3. Mix all the resulting Hypaque solution with all the resulting Ficoll solution.
4. Fill graduated cylinder with 250 ml. of the Ficoll-Hypaque solution.
5. Measure the sp-gr. of the solution with a hydrometer, if the specific gravity is less than 1.07–108, add more Hypaque solution, if it is greater than 1.08 add distilled $H_2O$.
6. Autoclave the solution.

In addition to maintaining the viability of, e.g., lymphocytes, the process of this invention permits the recovery of over 90% of the total cells, e.g., lymphocytes, present. This is due to the fact that the medium mixed with the anticlotting agent helps prevent clumping of the cells.

I claim:
1. A method of maintaining the viability of leukocytes which comprises (a) drawing blood form a patient or donor directly into a mixture of an anticlotting agent and a medium which sustains the viability of leukocytes, (b) separating the leukocytes by centrifugation onto a solution having a specific gravity of about the same as the leukocytes being separated containing a mixture of a water soluble synthetic copolymer of sucrose and epichlorohydrin with an average molecular weight of 400,000±100,000 and sodium ditrizoate, (c) collecting the leukocytes and placing them in containers having a medium which sustains the viability of the leukocytes, said medium containing antibiotics and a substance selected from the group consisting of heat-inactivated fetal calf serum and a serum substitute equivalent thereto.

2. The method of claim 1 wherein the anticlotting agent is heparin.

3. The method of claim 1 wherein the medium which sustains the viability of leukocytes is a basic salt solution.

4. The method of claim 1 wherein the medium which sustains the viability of leukocytes is a minimum essential medium.

5. The method of claim 1 wherein the leukocytes are lymphocytes and the specific gravity of the solution in step (b) is about 1.07 to 1.08.

* * * * *